United States Patent [19]

Wetzel et al.

[11] 4,401,667
[45] Aug. 30, 1983

[54] CEPHALOSPORINS

[75] Inventors: Bernd Wetzel; Eberhard Woitun, both of Biberach; Wolfgang Reuter, Laupertshausen; Roland Maier, Biberach; Uwe Lechner, Ummendorf; Hanns Goeth, Biberach, all of Fed. Rep. of Germany

[73] Assignee: Karl Thomae Gesellschaft mit beschränkter Haftung, Ingelheim am Rhein, Fed. Rep. of Germany

[21] Appl. No.: 323,432

[22] Filed: Nov. 20, 1981

[30] Foreign Application Priority Data

Dec. 13, 1980 [DE] Fed. Rep. of Germany ....... 3047082

[51] Int. Cl.³ .................. A61K 31/545; C07D 501/56
[52] U.S. Cl. ...................................... 424/246; 544/25; 544/27
[58] Field of Search ...................... 424/246; 544/27, 25

[56] References Cited
U.S. PATENT DOCUMENTS 4,258,184 3/1981 Kai et al. ............................... 544/27
4,311,699 1/1982 Haskell et al. ........................ 544/27
4,364,944 12/1982 Wetzel et al. ......................... 544/27

Primary Examiner—Paul M. Coughlan, Jr.
Attorney, Agent, or Firm—Hammond & Littell, Weissenberger & Muserlian

[57] ABSTRACT

Compounds of the formula

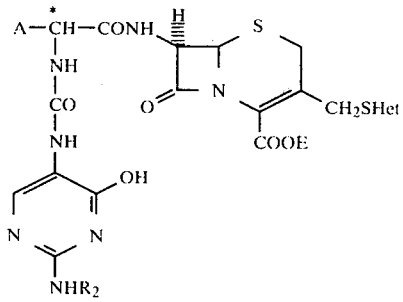

wherein
A is phenyl, 4-hydroxy-phenyl, 2-thienyl, 3-thienyl or 3,4-dihydroxy-phenyl;
Het is 4H-5,6-dioxo-1,2,4-triazin-3-yl, 4-methyl-5,6-dioxo-1,2,4-triazin-3-yl, 1-vinyl-tetrazol-5-yl, 1-allyl-tetrazol-5-yl or

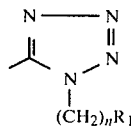

where
n is an integer from 1 to 3, inclusive,
$R_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group; or —$(CH_2)_n$—$R_1$ may also be alkyl of 2 to 4 carbon atoms or 2,3-dihydroxy-propyl;
$R_2$ is an unsubstituted or monosubstituted heterocyclic radical selected from the group consisting of 3-pyridyl, 5-pyrimidinyl, 2-thienyl, 2-furylmethyl, 2-thienylmethyl, 2-imidazolylmethyl, 2-thiazolylmethyl, 3-pyridylmethyl or 5-pyrimidinylmethyl, where the substituent is chlorine, methyl, acetylamino, hydroxyl, methylsulfinyl, methylsulfonyl, aminocarbonyl or aminosulfonyl; and
E is hydrogen or a protective group which is easily removable in vitro or in vivo;
and, when E is hydrogen, non-toxic, pharmacologically acceptable salts thereof formed with inorganic or organic bases; the compounds as well as their salts are useful as antibiotics.

11 Claims, No Drawings

CEPHALOSPORINS

This invention relates to novel cephalosporins and salts thereof, to methods of preparing these compounds, to pharmaceutical compositions containing them as active ingredients, and to methods of using them as antibiotics.

More particularly, the present invention relates to a novel class of cephalosporins represented by the formula

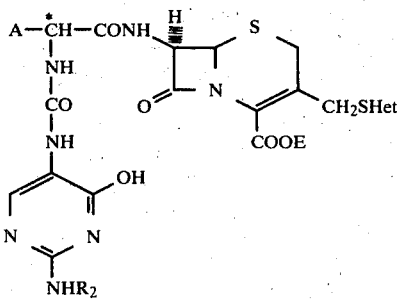

wherein
A is phenyl, 4-hydroxy-phenyl, 2-thienyl, 3-thienyl or 3,4-dihydroxy-phenyl;
Het is 4H-5,6-dioxo-1,2,4-triazin-3-yl, 4-methyl-5,6-dioxo-1,2,4-triazin-3-yl, 1-vinyl-tetrazol-5-yl, 1-allyl-tetrazol-5-yl or

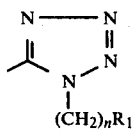

where
n is an integer from 1 to 3, inclusive,
$R_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group, or $-(CH_2)_n-R_1$ may also be alkyl of 2 to 4 carbon atoms or 2,3-dihydroxy-propyl;
$R_2$ is an unsubstituted or monosubstituted heterocyclic radical selected from the group consisting of 3-pyridyl, 5-pyrimidinyl, 2-thienyl, 2-furylmethyl, 2-thienylmethyl, 2-imidazolylmethyl, 2-thiazolylmethyl, 3-pyridylmethyl or 5-pyrimidinylmethyl, where the substituent is chlorine, methyl, acetylamino, hydroxyl, methylsulfinyl, methylsulfonyl, aminocarbonyl or aminosulfonyl; and
E is hydrogen or a protective group which is easily removable in vitro or in vivo, such as those which have heretofore been used in the field of penicillins and cephalosporins, especially ester-forming groups which can be removed by hydrogenation or hydrolysis or other treatments, or ester-forming groups which can easily be split off in the living organism;
and, when E is hydrogen, non-toxic, pharmacologically acceptable salts thereof formed with inorganic or organic bases, such as their alkali metal or alkaline earth metal salts, especially the sodium, potassium, magnesium or calcium salts; their ammonium salts; or their organic amine salts, such as the triethylamine or dicyclohexylamine salts.

In vitro easily removable protective groups are, for example, benzyl, diphenylmethyl, trityl, tert. butyl, 2,2,2-trichloroethyl or trimethylsilyl.

In vivo easily removable protective groups are, for example, alkanoyloxyalkyl, such as acetoxymethyl, propionyloxymethyl, 2-acetoxyethyl or pivaloyloxymethyl; or phthalidyl.

The asterisk above the carbon atoms in formula I indicates a center of asymmetry.

The cephalosporin compounds of the formula I and the intermediates described hereinafter exist in two tautomeric forms with respect to the pyrimidine ring, that is, the lactim and the lactam form. Which of the two forms I or I' is predominant, depends particularly on the respective solvent and on the type of substituent $-NHR_2$:

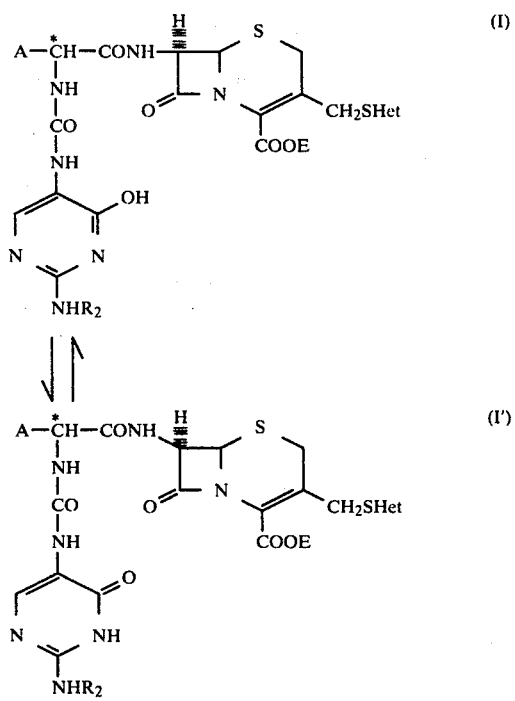

It goes without saying that the compounds of the formula I referred to above always comprise both tautomeric forms.

With regard to the chiral center C*, the compounds of the formula I may be present in the two possible R and S-configurations or as mixtures of these.

The compounds of the formula I may be prepared by the following methods.

Method A

By reacting a 7-amino-cephalosporanic acid compound of the formula

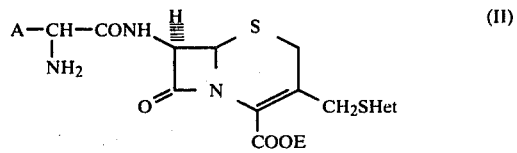

wherein A, Het and E have the meanings previously defined, with a pyrimidine derivative of the formula

wherein
R₂ has the meanings previously defined, and
B is —NCO or a derivative of —NHCOOH, such as —NHCOCl, —NHCOBr or

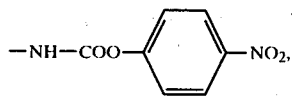

where —NHCOCl is especially preferred.

Also mixtures of such pyrimidine derivatives of the formula III can be used, wherein B has partly the one and partly the other of the above-mentioned meanings, for instance —NCO and —NHCOCl simultaneously.

The reaction is carried out in any desired mixture of water and those organic solvents which are miscible with water such as ketones, for example acetone; cyclic ethers, for example tetrahydrofuran or dioxane; nitriles, for example acetonitrile; formamides, for example dimethylformamide; dimethylsulfoxide; or alcohols, for example isopropanol; or in hexametapol. A mixture of tetrahydrofuran and water is particularly preferred. By addition of a base or by use of a buffer solution, the pH of the reaction mixture is kept in a pH range of about 2.0 to 9.0, preferably between pH 6.5 and 8.0.

Method B

By reacting a ureidocarboxylic acid of the formula

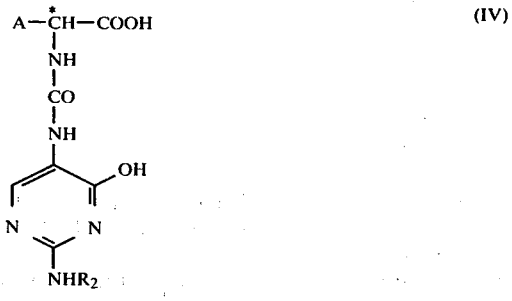

wherein A and R₂ have the meanings previously defined, or a salt or reactive derivative thereof, with a 7-aminocephalosporanic acid derivative of the formula

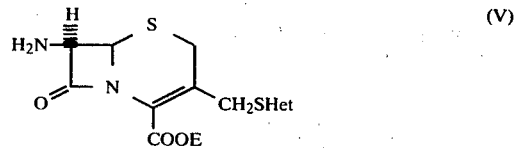

wherein E and Het have the meanings previously defined.

Suitable reactive derivatives of the ureidocarboxylic acids of the formula IV include, for example, their acid anhydrides such as those derived from chloroformates, for instance ethyl or isobutyl chloroformate, or their reactive esters such as the p-nitrophenyl ester or the N-hydroxysuccinimide ester, or their reactive amides such as the N-carbonyl-imidazole, but also their acid halides such as the corresponding acid chloride or their acid azide.

In principle, however, all methods of bonding which are known in β-lactam chemistry can be used.

The ureidocarboxylic acid or a salt or reactive derivative thereof is reacted with the 7-amino-cephalosporanic acid derivative in a solvent at temperatures between $-40°$ and $+40°$ C., optionally in the presence of a base. If, for example, an anhydride of the ureidocarboxylic acid, such as the anhydride with ethylchloroformate, is used, the reaction is carried out while cooling, for instance at $-10°$ to $+10°$ C., in the presence of a tertiary amine such as triethylamine or N,N-dimethylaniline, in a solvent such as acetone, tetrahydrofuran, dimethylformamide, chloroform, dichloromethane, hexametapol, or a mixture of these solvents. If, for example, an N-hydroxysuccinimide ester of the ureidocarboxylic acid is reacted with a derivative of the formula V, the reaction is preferably carried out at 0° to 20° C. in the presence of a base such as triethylamine, in a solvent such as dimethylformamide, dichloromethane, dioxane, or a mixture of such solvents.

The reaction of the ureidocarboxylic acid of the formula IV or a salt thereof with a compound of the formula V is advantageously carried out in the presence of a condensation agent, for instance in the presence of N,N'-dicyclohexylcarbodiimide.

Method C

By reacting a compound of the formula

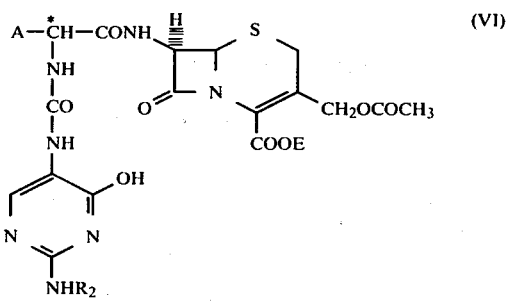

wherein
A and R₂ have the meanings previously defined, and
E is hydrogen,
with a compound of the formula

wherein
Het has the meanings previously defined, and
M is hydrogen, an alkali metal or an alkaline earth metal.

For example, a compound of the formula VI is reacted with 5-vinyl-2-mercapto-1,2,3,4-tetrazole in a solvent such as water, methanol, ethanol, acetone, methyl ethyl ketone, tetrahydrofuran, acetonitrile, ethyl acetate, dimethoxyethane, dimethylformamide, dimethyl sulfoxide, chloroform or a mixture of these solvents. Preferably, a strong polar solvent such as water or the like is used. In this case the pH of the reaction solution is advantageously maintained between 2 and 10, and particularly between 4 and 8. The desired pH value can be adjusted by addition of a buffer solution, such as sodium phosphate. The reaction conditions are not subject to special restrictions. Normally, the reaction is carried out at a temperature in a range of 0° to 100° C., over a reaction time of several hours.

The compounds of the formula I wherein E is other than hydrogen, prepared according to the above methods, can be treated in a manner known per se in order to separate the protecting group. In this way the compounds wherein E is hydrogen, which are the particularly preferred end products according to the present invention, are obtained. For example, a compound of the formula I wherein E is diphenylmethyl is treated in known manner with anisole and trifluoroacetic acid to separate the protective ester group, or a silyl protective group can be removed by aqueous hydrolysis, likewise in known manner.

The compounds of the formula I wherein E is a sodium or potassium cation are prepared by reacting the corresponding free acid of the formula I, i.e. wherein E is hydrogen, with the corresponding salt-forming ion. Suitable methods of doing this include, for example, the reaction with sodium ethyl hexanoate conventionally used in the chemistry of penicillins and cephalosporins, or the reaction with sodium bicarbonate and subsequent freeze-drying.

Moreover, the cephalosporin antibiotics of the formula I wherein E is hydrogen can be converted into the acyloxyalkyl esters, i.e. wherein E is, for example, a pivaloyoxymethyl radical

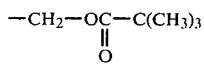

by reacting an alkali metal salt of the cephalosporin carboxylic acid, for example a sodium or potassium salt, with a pivaloyloxymethyl halide of the formula

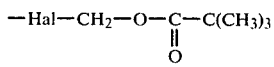

wherein Hal is chlorine, bromine or iodine.

Further suitable acyloxyalkyl halides are, for example, chloromethyl acetate, bromomethyl propionate or 1-bromoethyl acetate.

By using the corresponding starting compounds, it is possible to prepare the compounds of the formula I in the form of the individual isomers. If the end product is obtained in the D,L-form, the pure D- and L-diastereoisomers may be isolated by preparative liquid chromatogrphy (HPLC). The present invention includes the racemates and the isomers.

The ureidocarboxylic acids of the formula IV, the pyrimidines of the formula III and the cephalosporins of the formula VI are known from the literature. They are described in German Offenlegungsschrift No. 2,924,296.

The following examples illustrate the present invention and will enable others skilled in the art to understand it more completely. It should be understood, however, that the invention is not limited solely to the particular examples given below.

EXAMPLE 1

Sodium 7β-{D-α-[3-(2-(5′-aminosulfonyl-2′-thienylmethylamino)-4-hydroxy-5-pyrimidinyl)-ureido]-p-hydroxyphenylacetamideo}-3-{[1-(2′-hydroxyethyl)-tetrazol-5-yl]-thiomethyl}-ceph-3-em-4-carboxylate 2.72 gm (0.005 mol) of D-α-{3-[2-(5′-aminosulfonyl-2′-thienylmethylamino)-4-hydroxy-5-pyrimidinyl]-ureido}-p-hydroxyphenyl-acetic acid were dissolved in 30 ml of dry dimethylformamide. A solution of 2.62 gm (0.005 mol) of diphenylmethyl 7-amino-3-{[1-(2′-hydroxyethyl)-tetrazol-5-yl]-thiomethyl}-ceph-3-em-4-carboxylate in 30 ml of dry methylene chloride was added thereto. 1.13 gm of dicyclohexylcarbodiimide were added to this mixed solution, while cooling with ice, and the mixture was stirred for 2 hours at 10° C. and then for 6 hours at room temperature. Thin-layer chromatography showed that the starting compounds had almost totally disappeared. The mixture was filtered, the filtrate was evaporated to dryness in vacuo, and the residue was stirred twice with 50 ml of methanol and once with 100 ml of methylene chloride. The solid product thus obtained was suction-filtered off and washed thoroughly with ether. To remove any slight impurities left at the starting spot in the thin-layer chromatogram (methylene chloride:methanol 4:1), the product was chromatographed on a silicagel column. Yield of ester: 3.46 gm (65.6% of theory).

The product thus obtained was suspended in a little methylene chloride and, while cooling with ice, stirred for 30 minutes with 2 ml of anisole and 10 ml of trifluoroacetic acid, during which time it dissolved. Subsequently, two batches of 50 ml of toluene were added, and the mixture was evaporated to dryness in vacuo after each addition. Ether was added to the residue, and the product was suction-filtered off.

To prepare the sodium salt, the product was dissolved in a little dimethylformamide, the calculated amount of sodium ethyl hexanoate in methanol was added, and the mixture was mixed with ether. The precipitate formed thereby was suction-filtered off, carefully washed with ether and dried in vacuo. Yield of sodium salt (based on the cephalosporin derivative used): 2.71 gm (61% of theory). IR-spectrum: 1760, 1655, 1615, 1550 cm$^{-1}$. NMR-spectrum (DMSO+CD$_3$OD) signals at ppm: 3.55 (m, 2H), 3.75 (m, 2H), 4.2–4.6 (m, 2+2+2H), 4.90 (d, 1H), 5.45 (s, 1H), 5.65 (d, 1H), 6.75 (d, 2H), 7.0 (d, 1H), 7.25 (d, 2H), 7.40 (d, 1H), 8.15 (s, 1H).

The cephalosporins (sodium salts) of the formula I shown in the following table were synthesized in analogous manner:

| Example | A | R₂ | SHet | IR-Spectrum cm⁻¹ | NMR-Signals (DMSO + CD₃OD) Signals at ppm: |
|---|---|---|---|---|---|
| 2 | 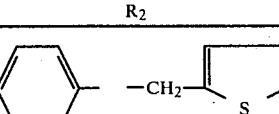 | 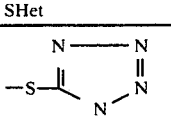 | 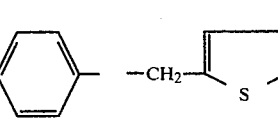 | 1760<br>1655<br>1155 | 3.55 (m, 2H), 4.30 (m, 4H), 4.95 (d, 1H),<br>5.35–5.90 (m, 4H), 6.65–7.0 (m, 4H),<br>7.25 (d, 2H), 7.40 (d, 1H), 8.15 (s, 1H). |
| 3 | 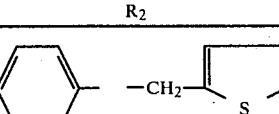 | 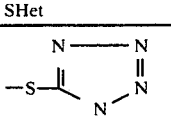 | 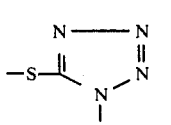 | 1760<br>1640 | 3.0 (m, 2H), 3.55 (m, 2H), 4.25 (m, 4H),<br>5.0 (d, 1H), 5.45 (s, 1H), 5.65 (d, 1H),<br>6.75 (d, 2H), 6.95 (d, 1H), 7.25 (d, 2H),<br>7.40 (d, 1H), 8.10 (s, 1H). |
| 4 | 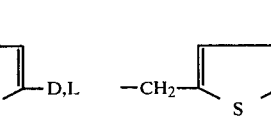 | 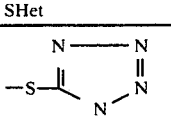 | 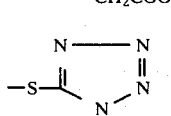 | 1765<br>1660 | 3.55 (m, 2H), 3.80 (m, 2H), 4.2–4.6 (m,<br>6H), 4.95 (dd, 1H), 5.55 (dd, 1H), 5.75 (s,<br>broad, 1H), 7.0 (m, 4H), 7.3–7.5 (m, 2H),<br>8.15 (s, 1H) |
| 5 | 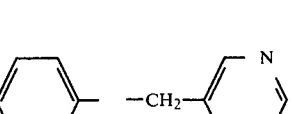 | 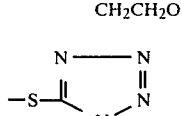 | 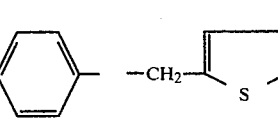 | 1760<br>1655 | 3.60 (m, 2H), 4.70 (m, 4H), 4.95 (d, 1H),<br>5.30–5.90 (m, 4H), 6.75 (d, 2H), 7.30 (m,<br>3H), 7.7 (m, 1H), 8.1 (s, 1H), 8.5 (m, 2H). |

EXAMPLE 6

Sodium 7-{D-α-[3-(2-(5'-aminosulfonyl)-2'-thienylmethylamino)-4-hydroxy-5-pyrimidinyl)-ureido]-p-hydroxy-phenylacetamido}-3-{[1-(2'-aminoethyl)-tetrazol-5-yl]-thiomethyl}-ceph-3-em-4-carboxylate This compound was prepared analogous to Example 1, starting from the ureidocarboxylic acid used therein and an equimolar amount of diphenylmethyl 7-amino-3-{[1-(2'-t-butoxycarbonylaminoethyl)-tetrazol-5-yl]-thiomethyl}-ceph-3-em-4-carboxylate. Yield after splitting off the protective groups and preparation of the sodium salt: 43.5% of theory.

IR-spectrum: 1760, 1675, 1600 cm⁻¹.

NMR-spectrum (DMSO+CD₃OD) signals at ppm: 3.15 (m, 2H), 3.55 (m, 2H), 4.35 (m, 6H), 4.95 (d, 1H), 5.55 (s, 1H), 5.70 (d, 1H), 6.75 (d, 2H), 7.05 (d, 1H), 7.25 (d, 2H), 7.4 (d, 1H), 8.15 (s, 1H).

EXAMPLE 7

Sodium 7-{D-α-[3-(4-hydroxy-2-(4'-methyl-2'-imidazolylmethylamino)-5-pyrimidinyl)-ureido]-p-hydroxy-phenylacetamido}-3-{[1-(2'-acetylaminoethyl)-tetrazol-5-yl]thiomethyl}-ceph-3-em-4-carboxylate 0.2 gm of N-methyl-morpholine were added to a solution of 830 mg (0.002 mol) of D-α-{3-[4-hydroxy-2-(4'-methyl-2'-imidazolylmethylamino)-5-pyrimidinyl]-ureido}-p-hydroxyphenyl-acetic acid in 20 ml of dry dimethylformamide. The solution was cooled to −15° C., and at this temperature a solution of 0.22 gm of ethyl chloroformate in 5 ml of methylene chloride was added dropwise. The mixture thus obtained was kept at this temperature for 45 minutes.

Then, at −15° C., a solution of 1.12 gm (0.002 mol) of diphenylmethyl 7-amino-3{[1-(2'-acetylaminoethyl)-tetrazol-5-yl]-thiomethyl}-ceph-3-em-4-carboxylate in 20 ml of dry methylene chloride was added dropwise. The mixture was stirred for one hour at −10° C. and then allowed to return slowly to room temperature. The resulting solution was evaporated to dryness in vacuo, and the residue was further treated as described in Example 1. The protective ester group was also split off analogous to Example 1. Yield of sodium salt: 900 mg (54% of theory).

IR-spectrum: 1760, 1650, 1610, 1550 cm⁻¹.

NMR-spectrum (DMSO+CD₃OD) signals at ppm: 1.85 (s, 3H), 2.1 (s, 3H), 3.6 (m, 2+2H), 4.2–4.5 (m, 2+2+2H), 5.05 (d, 1H), 5.45 (s, 1H), 5.65 (d, 1H), 6.75 (m, 2+1H), 7.25 (d, 2H), 8.10 (s, 1H).

EXAMPLE 8

7-{D-α-[3-(2-(5'-aminosulfonyl-2'-thienylmethylamino)-4-hydroxy-5-pyrimidinyl)-ureido]-p-hydroxyphenylacetamido}-3-[(1-hydroxysulfonylmethyl-tetrazol-5-yl)-thiomethyl]-ceph-3-em-4-carboxylic acid From 495 mg (0.001 mol) of the ureidocarboxylic acid used in Example 1, an activated anhydride solution was prepared analogous to Example 7 with N-methyl-morpholine and ethyl-chloroformate. Separately, 600 mg of N,O-bis-trimethylsilyl-acetamide were added to a suspension of 410 mg (0.001 mol) of 7-amino-3-[(1-hydroxysulfonyl-methyltetrazol-5-yl)-thiomethyl]-ceph-3-em-4-carboxylic acid in 20 ml of anhydrous acetonitrile, whereby a solution was obtained. This solution was cooled to −15° C., and at this temperature it was added dropwise to the activated anhydride solution above referred to. The mixture was then stirred at −10° C. for one hour and then at +10° C. for one hour. Thereafter, 2 ml of methanol were added, and the mixture was filtered to remove insoluble matter. Then, the solvent was evaporated in vacuo. The residue was taken up in 40 ml of water, and the solution was adjusted to pH 7.0. At this pH value, the product was extracted twice with ethyl acetate. The aqueous phase was adjusted to pH 2.9 with dilute hydrochloric acid while cooling with ice, and the precipitate formed thereby was suction-filtered off, washed with a little water and dried in vacuo.

Yield: 445 mg (57% of theory).

IR-spectrum: 1760, 1660, 1600 cm$^{-1}$.

NMR-spectrum (DMSO+CD$_3$OD) signals at ppm: 3.60 (m, 2H), 4.25–4.45 (m, 4H), 5.0 (m, 3H), 5.55 (s, 1H), 5.70 (d, 1H), 6.75 (d, 2H), 7.0 (d, 1H), 7.25 (d, 2H), 7.45 (d, 1H), 8.15 (s, 1H).

The following cephalosporins of the formula I were synthesized analogous to Examples 7 and 8:

thylamino)-4-hydroxy-5-pyrimidinyl)-ureido]-p-hydroxy-phenylacetamido}-3-acetoxymethyl-ceph-3-em-4-carboxylic acid were obtained.

500 mg of this cephalosporin were heated at 70° C. in 20 ml of a phosphoric acid buffer solution, pH 6.3, together with 200 mg of 1-(2'-dimethylaminoethyl)-5-mercaptotetrazole, for 6 hours in a nitrogen atmosphere, the pH being maintained at between 6 and 6.5. Thereafter, the reaction mixture was cooled, filtered to remove insoluble matter, and extracted twice with ethyl acetate. Then, hydrochloric acid was added, while cooling, to give a pH of 2.8. The precipitate formed thereby was suction-filtered off, washed with a little

| Example | A | R$_2$ | SHet | IR-Spectrum cm$^{-1}$ | NMR-Spectrum (DMSO + CD$_3$OD) Signals at ppm: |
|---|---|---|---|---|---|
| 9 | HO–⟨⟩– | –CH$_2$–furan | –S–tetrazole–CH$_2$CH$_2$NHCONH$_2$ | 1760, 1660 | 3.0 (m, 2H), 3.6 (m, 2H), 4.2–4.5 (m, 6H), 4.95 (d, 1H), 5.4 (s, 1H), 5.65 (d, 1H), 6.3 (m, 2H), 6.75 (d, 2H), 7.25 (d, 2H), 7.45 (s, 1H), 8.1 (s, 1H). |
| 10 | HO–⟨⟩– | –CH$_2$–pyridyl | –S–tetrazole–CH$_2$CH$_2$OH | 1760, 1650, 1610 | 3.55 (m, 2H), 3.8 (m, 2H), 4.2–4.5 (m, 6H), 4.95 (d, 1H), 5.40 (s, 1H), 5.6 (d, 1H), 6.75 (d, 2H), 7.25 (m, 3H), 7.65 (m, 1H), 8.1 (s, 1H), 8.45 (m, 2H). |
| 11 | HO–⟨⟩– | –CH$_2$–(methylimidazolyl, NH) | –S–tetrazole–CH$_2$CH$_2$CONH$_2$ | 1760, 1665, 1600 | 2.1 (s, 3H), 2.5 (m, 2H), 3.60 (m, 2H), 4.3 (m, 6H), 5.0 (d, 1H), 5.40 (s, 1H), 5.60 (d, 1H), 6.75 (m, 3H), 7.25 (d, 2H), 8.05 (s, 1H). |
| 12 | HO–⟨⟩– | –CH$_2$–(methylimidazolyl, NH) | –S–tetrazole–C$_2$H$_5$ | 1760, 1650 | 1.0 (t, 3H), 2.05 (s, 3H), 3.55 (m, 2H), 4.3 (m, 6H), 4.90 (d, 1H), 5.40 (s, 1H), 5.65 (d, 1H), 6.7–6.9 (m, 2 + 1H), 7.25 (d, 2H), 8.10 (s, 1H). |
| 13 | HO–⟨⟩– | –pyridyl-SO$_2$NH$_2$ | –S–tetrazole–CH$_2$CH$_2$OH | 1760, 1660 | 3.5 (m, 2H), 4.3 (m, 6H), 4.95 (d, 1H), 5.45 (s, 1H), 5.65 (d, 1H), 6.75 (d, 2H), 7.25 (d, 2H), 7.4 (m, 1H), 8.05 (s, 1H), 8.2 (m, 2H). |
| 14 | HO–⟨⟩– | –pyridyl-SO$_2$NH$_2$ | –S–tetrazole–CH$_2$CONH$_2$ | 1760, 1655 | 3.65 (m, 2H), 4.3–4.8 (m, 4H), 4.95 (d, 1H), 5.45 (s, 1H), 5.65 (d, 1H), 6.75 (d, 2H), 7.25 (d, 2H), 7.4 (m, 1H), 8.05 (s, 1H), 8.2 (m, 2H). |

EXAMPLE 15

Sodium 7-{D-α-[3-(2-(5'-aminosulfonyl-2'-thienylmethylamino)-4-hydroxy-5-pyrimidinyl)-ureido]-p-hydroxy-phenylacetamido}-3-{[1-(2'-dimethylaminoethyl)tetrazol-5-yl]-thiomethyl}-ceph-3-em-4-carboxylate Starting from 2.72 gm of D-α-{3-[2-(5'-aminosulfonyl-2'-thienylmethylamino)-4-hydroxy-5-pyrimidinyl]-ureido}-p-hydroxy-phenylacetic acid (0.005 mol) and 1.36 gm of 7-aminocephalosporanic acid, 2.08 gm (57%) of 7-{D-α-[3-(2-(5'-aminosulfonyl-2'-thienylmethylwater and dried. The residue was converted into the sodium salt in the usual way.

Yield: 64% of theory.

IR-spectrum: 1760, 1660, 1600 cm$^{-1}$.

NMR-spectrum (DMSO+CD$_3$OD) signals at ppm: 2.35 (s, 6H), 2.80 (m, 2H), 3.60 (m, 2H), 4.30 (m, 6H), 4.95 (d, 1H), 5.45 (s, 1H), 5.65 (d, 1H), 6.75 (d, 2H), 7.05 (d, 1H), 7.30 (d, 2H), 7.45 (d, 1H), 8.15 (s, 1H).

EXAMPLE 16

Sodium 7β-{D-α-[3-(2-(5'-aminosulfonyl-2'-thienylmethylamino)-4-hydroxy-5-pyrimidinyl)-ureido]-p-hydroxyphenylacetamido}-3-[(1-methyl-5,6-dioxo-1,3,4-triazin-2-yl)thiomethyl]-ceph-3-em-4-carboxylate This compound was synthesized analogous to Example 15, starting from the cephalosporin derivative used therein and 4-methyl-2-mercapto-5,6-dioxo-1,3,4-triazine.

Yield: 66.5% of theory.

IR-spectrum: 1760, 1670, 1600 cm$^{-1}$.

NMR-spectrum (DMSO+CD$_3$OD) signals at ppm: 3.55 (m, 2H+s, 3H), 4.35 (m, 4H), 4.90 (d, 1H), 5.50 (s, 1H), 5.65 (d, 1H), 6.75 (d, 2H), 7.05 (d, 1H), 7.25 (d, 2H), 7.40 (d, 1H), 8.15 (s, 1H).

The compounds of the formula I shown in the following table were prepared in analogy to Example 15:

lubricants, dyes, fibers, leather, paper and wood, as well as foodstuffs.

This is made possible by the fact that the compounds of the present invention are highly active, both in vitro and in vivo, against harmful microorganisms, particularly against gram-positive and gram-negative bacteria and bacteria-like microorganisms, being distinguished in particular by a broad spectrum of activity.

Many local and/or systemic bacterial diseases can be treated and/or prevented by use of these cephalosporin derivatives of the present invention. Examples of such diseases include but are not limited to those caused by the following microorganisms:

Micrococcaceae, such as staphylococci;
Lactobacteriaceae, such as streptococci;
Corynebacteriaceae, such as corynebacteria;
Enterobacteriaceae, such as escherichiae bacteria of the coli group;
Klebsiella bacteria, such as K. pneumoniae;

| Example | A | R$_2$ | SHet | IR-Spectrum cm$^{-1}$ | NMR-Spectrum (DMSO + CD$_3$OD) Signals at ppm: |
|---|---|---|---|---|---|
| 17 | HO–⌬– | –CH$_2$–(furan) | –S–(triazinone)–CH$_2$NHSO$_3$H | 1760, 1655, 1600 | 3.55 (m, 2H), 4.35 (m, 4H), 4.8–5.1 (m, 2 + 1H), 5.4 (s, 1H), 5.6 (d, 1H), 6.25 (m, 2H), 6.75 (d, 2H), 7.25 (d, 2H), 7.40 (s, broad, 1H), 8.10 (s, 1H). |
| 18 | HO–⌬– | –CH$_2$–(pyrrole-CH$_3$) | –S–(triazinone)–CH$_2$CONH$_2$ | 1760, 1650, 1610 | 2.15 (s, 3H), 3.65 (m, 2H), 4.35–4.80 (m, 6H), 4.95 (d, 1H), 5.35 (s, 1H), 5.60 (d, 1H), 6.75 (m, 3H), 7.25 (d, 2H), 8.10 (s, 1H). |
| 19 | HO–⌬– | –CH$_2$–(pyrrole-CH$_3$) | –S–(triazinone)–CH$_2$CH$_2$SO$_2$CH$_3$ | 1760, 1660, 1155 | 2.15 (s, 3), 2.85 (s, 3H), 3.5–3.8 (m, 4H), 4.3 (m, 6H), 4.95 (d, 1H), 5.40 (s, 1H), 5.60 (d, 1H), 6.75 (m, 3H), 7.25 (d, 2H), 8.10 (s, 1H). |
| 20 | HO–⌬– | –CH$_2$–(pyridine) | –S–(triazinone)–CH$_2$CH$_2$NHSO$_2$NH$_2$ | 1760, 1660, 1150 | 3.1–3.7 (m, 4H), 4.4 (m, 6H), 5.0 (d, 1H), 5.45 (s, 1H), 5.65 (d, 1H), 6.75 (d, 2H), 7.25 (m, 3H), 7.65 (m, 1H), 8.1 (s, 1H), 8.50 (m, 2H). |

The compounds of the present invention, that is, thos embraced by formulas I and I' and their non-toxic, pharmacologically acceptable salts, have useful pharmacodynamic properties. More particularly, they exhibit very effective antibacterial activity in warm-blooded animals, such as mice.

Furthermore, the compounds according to the present invention are very well compatible. Therefore they are useful for the prophylaxis and chemotherapy of local and systemic infections in both human and veterinary medicine.

Thus, for example, these compounds are useful for the treatment of diseases of the respiratory tract, the pharyngeal cavity and urinary tract, particularly pharyngitis, pneumonia, peritonitis, pyelonephritis, otitis, cystitis, endocarditis, bronchitis, arthritis and general systemic infections. Moreover, these compounds are useful as preservatives for inorganic or organic materials, especially for organic materials such as polymers, Proteae bacteria of the proteus group, such as proteus vulgaris;
Salmonella bacteria, such as thyphimurium;
Shigella bacteria, such as shigella dysenteriae;
Pseudomonas bacteria, such as pseudomonas aeruginosa;
Aeromonas bacteria, such as aeromonas lique faciens;
Spirillaceae such as vibrio bacteria, such as vibrio cholerae;
Parvobacteriaceae or brucellaceae, such as pasteurella bacteria;
Brucella bacteria, such as brucella abortus;
Neisseriaceae, such as neisseria;
Haemophilus bacteria, such as haemophilus influenza;
Bordatella bacteria, such as bordatella pertussis;
Moraxella bacteria, such as moraxella lacunata;
Bacteroidaceae, such as bacteroides bacteria;

Fusiforme bacteria, such as fusobacterium fusiforme;
Sphaerophorus bacteria, such as sphaerophorus necrophorus;
Bacillaceae, such as aerobic spore formers, like bacillus antracis;
Anerobe spore formers chlostridia, such as chlostridium perfringens;
Spirochaetaceae, such as borrelia bacteria;
Treponema bacteria, such as treponema palladium; and
Leptospira bacteria, such as leptospira interrogans.

Specific examples of compounds of the present invention, which exhibit broad spectrum antibacterial activity are the following:

Sodium 7β-{D-α-[3-(4-hydroxy-2-(3'-pyridylmethylamino)-5-pyrimidinyl)-ureido]-p-hydroxyphenylacetamido}-3-{[1-(2'-hydroxyethyl)-tetrazol-5-yl]-thiomethyl}-ceph-3-em-4-carboxylate, Sodium 7β-{D-α-[3-(2-(5'-aminosulfonyl-2'-thienylmethylamino)-4-hydroxy-5-pyrimidinyl)-ureido]-p-hydroxyphenylacetamido}-3-{[1-(2'-hydroxyethyl)-tetrazol-5-yl]-thiomethyl}-ceph-3-em-4-carboxylate, Sodium 7β-{D-α-[3-(2-(5'-aminosulfonyl-2'-thienylmethylamino)-4-hydroxy-5-pyrimidinyl)-ureido]-p-hydroxyphenylacetamido}-3-[(1-vinyl-tetrazol-5-yl)-thiomethyl]-ceph-3-em-4-carboxylate, Sodium 7β-{D,L-α-[3-(2'(5'-aminosulfonyl-2'-thienyl methylamino)-4-hydroxy-5-pyrimidinyl)-ureido]-2-thienylacetylamido}-3-{[1-(2'-hydroxyethyl)-tetrazol-5-yl]-thiomethyl}-ceph-3-em-4-carboxylate, Sodium 7β-{D-α-[3-(4-hydroxy-2-(4'-methyl-2'-imidazolyl-methylamino)-5-pyrimidinyl)-ureido]-p-hydroxyphenyl-acetamido}-3-{[1-(2'-hydroxyethyl)-tetrazol-5-yl]thiomethyl}-ceph-3-em-4-carboxylate, Sodium 7β-{D-α-[3-(2-(5'-aminosulfonyl-2'-thienyl methylamino)-4-hydroxy-5-pyrimidinyl)-ureido]-p-hydroxyphenylacetamido}-3-{[1-(2'-aminocarbonylethyl)-tetrazol-5-yl]-thiomethyl}-ceph-3-em-4-carboxylate, and Sodium 7β-{D-α-[3-(2-(2'-furylmethylamino)-4-hydroxy-5-pyrimidinyl)-ureido]-p-hydroxyphenylacetamido}-3-{[1-(2'-methyl-sulfonylethyl)-tetrazol-5-yl]-thiomethyl}-ceph-3-em-4-carboxylate.

The antibiotic activities of the compounds of the present invention were ascertained by the following test methods:

1. In vitro tests

The tests were performed using the serial dilution test in the microtiter system. The effect of the test compound on bacteriostasis was tested in a liquid medium at the following concentrations: 128, 64, 32, 16, 8, 4, 2, 1, 0.5, 0.25, 0.12 and 0.06 μgm/ml. The nutrient medium consisted of 10 gm of peptone, 8 gm of meat extract oxoid, 3 gm of sodium chloride, and 2 gm of sec. sodium phosphate diluted with distilled water to 100 ml (pH 7.2–7.4). The age of the primary cultures was approximately 20 hours. The standardization of the bacteria suspension was effected using a photometer according to the method of Eppendorf (test tube φ 14 mm, filter 546 nm), using for comparison a barium sulfate suspension formed by the addition of 3.0 ml of 1% barium chloride solution to 97 ml of 1% sulfuric acid. After standardization, the test microorganisms were further diluted to a concentration of 1:1500, using a sodium chloride solution.

16 mgm of the particular test compound were put into a 10 ml measuring flask, and the flask was subsequently filled to the mark with the solvent. The further dilution series was standardized with distilled water or the appropriate solvent.

The depressions of the microtiter plates were filled with 0.2 ml of nutrient medium. 0.01 ml of the appropriate test compound solution was then added, followed by inoculation with 0.01 ml (1 drop) of the standardized bacteria suspension. The bacteria were incubated at 37° C. for 18 to 20 hours. Control tests using only the solvent were carried out simultaneously.

The readings were made macroscopically to determine the minimum inhibitory concentration (the lowest still bacteriostatically effective concentration).

The following test organisms were used:
Staphylococcus aureus SG 511, Escherichia coli ATCC 11 775, Pseudomonas aeruginosa hamburgensis and Pseudomonas aeruginosa BC 19, Serratia marcescens ATCC 13 880, Klebsiella pneumoniae ATCC 10 031 and BC 6, Proteus mirabilis BC 17, Proteus rettgeri BC 7, Enterobacter Cloaceae ATCC 13047 and E. coli R+TEM (β-lactamase carrier).

Table 1 below shows the minimum inhibiting concentration (MIC) determined for typical representatives of the compounds according to the invention, where Sodium 7β-{D-α-[3-(4-hydroxy-2-(3'-pyridylmethylamino)-5-pyrimidinyl)-ureido]-p-hydroxyphenylacetamido}-3-{[1-(2'-hydroxyethyl)-tetrazol-5-yl]-thiomethyl}-ceph-3-em-4-carboxylate=compound A, Sodium 7β-{D-α-[3-(2-(5'-aminosulfonyl-2'-thienylm ethylamino)-4-hydroxy-5-pyrimidinyl)-ureido]-p-hydroxyphenylacetamido}-3-{]1-(2'-hydroxyethyl)-tetrazol-5-yl]-thiomethyl}ceph-3-em-4-carboxylate=compound B, Sodium 7β-{D-α-[3-(2-(5'-aminosulfonyl-2'-thienylmethylamino)-4-hydroxy-5-pyrimidinyl)-ureido]-p-hydroxyphenylacetamido}-3-{[1-(2'-aminocarbonylethyl)-tetrazol-5-yl]-thiomethyl}ceph-3-em-4-carboxylate=compound C, and Sodium 7β-{D-α-[3-(2-(2'-furylmethylamino)-4-hydroxy-5-pyrimidinyl)-ureido]-p-hydroxyphenylacetamido}-3-{[1-(2'-methylsulfonylethyl)tetrazol-5-yl]-thiomethyl}-ceph-3-em-4-carboxylate=-compound D, in comparison to the known cephalosporin cefuroxim.

TABLE 1

| | MIC values μg/ml | | | | | | | | | | |
|---|---|---|---|---|---|---|---|---|---|---|---|
| Compound | Staph. aureus SG 511 | E. coli ATCC 11775 | Pseud. Hbg. | Pseud. BC 19 | Serr. marcesc. ATCC 13880 | Kl. pneum. ATCC 10031 | Kl. pneum. BC 6 | Prot. mirab. BC 17 | Prot. retg. | Ent. cloacaeae ATCC 13047 | E. coli R + TEM |
| A | 1 | 0.12 | 8 | 4 | 0.25 | 0.25 | 0.5 | 0.12 | 0.5 | 0.5 | 8 |
| B | 1 | 0.06 | 4 | 2 | 0.25 | 0.12 | 0.25 | 0.12 | 0.25 | 0.25 | 4 |
| C | 1 | 0.12 | 4 | 4 | 0.5 | 0.25 | 0.25 | 0.25 | 0.5 | 0.25 | 4 |
| D | 0.5 | 0.25 | 8 | 8 | 0.5 | 0.25 | 0.5 | 0.25 | 1 | 0.5 | 8 |
| Cefuroxim | 1 | 8 | >128 | >128 | 8 | 2 | 4 | 0.5 | 2 | 32 | 4 |

The acute toxicity was determined by oral and subcutaneous administration of the compounds of Table 2 below at increasing doses to white laboratory mice.

The $LD_{50}$ is the dose which results in the death of 50% of the animals within 8 days. All of the compounds had an $LD_{50}$ of more than 4 gm/kg when administered orally and an $LD_{50}$ of more than 2 gm/kg when administered subcutaneously. The compounds are therefore practically non-toxic.

Test compounds A-D of the invention and cefuroxim were tested in vivo against experimental infections in mice. *E.coli* ATCC 11 775 was used as the pathogenic bacteria. An intraperitoneal infection was induced with 0.2 ml of a 5% mucin suspension of the bacteria. This corresponds to approximately $1.4 \times 10^6$ E. coli bacteria per mouse. Female mice of the NMRI strain were divided into groups of 10 animals, of which 2 groups remained untreated while the remaining groups were treated with various doses of the particular cephalosporins according to the invention for the purpose of determining the $ED_{50}$ (dose at which 50% of the animals survive). The treatment was applied once (1 hour after infection). The observation period was 7 days. The results of these tests are shown in Table 2 below.

TABLE 2

| In vivo activity in mice *E. coli* infection (s.c. administration) | |
|---|---|
| Compound | $ED_{50}$ (mg/kg) |
| A | 0.9 |
| B | 0.4 |
| C | 0.7 |
| D | 1-2 |
| Cefuroxim | >100 |

For pharmaceutical purposes the compounds of the present invention are administered to warm-blooded animals perorally, parenterally, topically or rectally as active ingredients in customary pharmaceutical compositions, that is, compositions consisting essentially of an inert pharmaceutical carrier and an effective amount of the active ingredient, such as tablets, coated tablets, capsules, granulates, suppositories, solutions, suspensions, emulsions, ointments, gels, creams, powders and sprays. The active ingredient or a mixture of different active ingredients of the formula I may be administered to both humans and animals. The daily dose is from 5 to 500 mgm/kg, preferably from 10 to 200 mgm/kg, bodyweight at intervals of 24 hours, optionally administered in the form of several single doses. A single dose will preferably contain the active ingredient according to the invention in amount of from 1 to 250, especially 10 to 60 mgm/kg body weight. Depending on the type and body weight of the patient to be treated, on the type and severity of the disease, on the type of preparation and on the route of administration as well as on the period or interval over which the administration takes place, it may, however, be necessary to deviate from the above dosages. Thus, it may be sufficient to some cases to administer less than the above-mentioned amount of active ingredient, while in other cases the above-mentioned amount of active ingredient must be exceeded. The optimum dosage and route of administration of the active ingredients which are necessary in each case can easily be determined by one skilled in the art.

If the new compounds are used as additives for animal feed, they can be administered in the usual concentrations and preparations together with the feed or with feed preparations or with drinking water. By means of such administration the infection by gram-negative or gram-positive bacteria can be prevented, improved and/or cured, and also a promotion of the growth and an improvement in the utilization of the feed can be achieved.

The compounds of the formulas I and I' can be incorporated as active ingredients into the usual pharmaceutical preparations such as tablets, coated tablets, capsules or ampules. The single dose for adults is generally between 50 and 1000 mgm, preferably 100 to 500 mgm, the daily dose being between 100 and 4000 mgm, preferably 250 to 2000 mgm.

EXAMPLE 21

Tablets containing sodium
7β-{D-α-[3-(4-hydroxy-2-(3'-pyridylmethylamino)-5-pyrimidinyl)-ureido]-p-hydroxyphenylacetamido}-3-{[1-(2'-hydroxyethyl)-tetrazol-5-yl]-thiomethyl}-ceph-3-em-4-carboxylate A mixture consisting of 2 kg of active substance, 5 kg of lactose, 1.8 kg of potato starch, 0.1 kg of magnesium stearate and 0.1 kg of talcum is compressed to form tablets in the usual way, each tablet containing 200 mgm of active ingredient.

EXAMPLE 22

Coated tablets containing sodium
7β-{D-α-[3-(4-hydroxy-2-(3'-pyridyl-methylamino)-5-pyrimidinyl)-ureido]-p-hydroxyphenylacetamido}-3-{[1-(2'-hydroxyethyl)-tetrazol-5-yl]thiomethyl}-ceph-3-em-4-carboxylate Compressed tablets are produced according to Example 21, and they are then coated in the usual way with a coating consisting of sugar, potato starch, talcum and tragacanth.

EXAMPLE 23

Capsules containing sodium
7β-{D-α-[3-(4-hydroxy-2-(3'-pyridylmethylamino)-5-pyrimidinyl)-ureido]-p-hydroxyphenylacetamido}-3-{[1-(2'-hydroxyethyl)-tetrazol-5-yl]-thiomethyl}-ceph-3-em-4-carboxylate 5 kg of active substance are packaged in hard gelatine capsules in the usual way, each capsule containing 500 mg of the active substance.

EXAMPLE 24

Dry ampules containing sodium
7β-{D-α-[3-(4-hydroxy-2-(3'-pyridylmethylamino)-5-pyrimidinyl)-ureido]-p-hydroxyphenylacetamido}-3-{[1-(2'-hydroxyethyl)-tetrazol-5-yl]thiomethyl}-ceph-3-em-4-carboxylate Under aseptic conditions, 250 gm of active substance are dissolved in 200 ml of distilled water for injection. The solution is filtered through a Millipore filter (pore size 0.22 μm). The solution is filled into 1000 vials (capacity 10 ml) in amounts of 2.0 ml, and then lyophilized. The vials are then sealed with a rubber stopper and aluminum cap. In this way, vials (A) were obtained, each containing 250 mgm of active substance.

A physiological common salt solution for injection is filled into ampules in amounts of 2.0 ml, and the ampules are sealed. In this way, ampules (B) are obtained. The physiological common salt solution in ampules (B) is poured into the vials (A), thus producing an injectable solution for intravenous administration.

Distilled water for injection is poured into the vials (A) in amounts of 20 ml, and the solution is dissolved in a 5% solution of glucose for injections (250 ml). In this way, solutions for continuous infusions are prepared.

Any one of the other compounds embraced by formula I or a non-toxic, pharmacologically acceptable salt thereof may be substituted for the particular active ingredient in Examples 21 through 24. Likewise, the amount of active ingredient in these illustrative examples may be varied to achieve the dosage unit range set forth above, and the amounts and nature of the inert pharmaceutical carrier ingredient may be varied to meet particular requirements.

While the present invention had been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

[Structure 1: A—CH—CONH-[β-lactam-cephem]-CH$_2$SHet with NH-CO-NH-[pyrimidinyl with OH and NHR$_2$], COOE]

or

[Structure 2: similar with =O instead of OH on pyrimidinyl ring]

wherein
A is phenyl, 4-hydroxy-phenyl, 2-thienyl, 3-thienyl or 3,4-dihydroxy-phenyl;
Het is 4H-5,6-dioxo-1,2,4-triazin-3-yl, 4-methyl-5,6-dioxo-1,2,4-triazin-3-yl, 1-vinyl-tetrazol-5-yl, 1-allyl-tetrazol-5-yl or

[Structure: tetrazole ring with (CH$_2$)$_n$R$_1$ substituent]

where
n is an integer from 1 to 3, inclusive,
R$_1$ is hydroxyl, amino, dimethylamino, acetylamino, aminocarbonyl, aminocarbonylamino, aminosulfonyl, aminosulfonylamino, methylcarbonyl, methylsulfonylamino, cyano, hydroxysulfonylamino, methylsulfonyl, methylsulfinyl, a carboxylic acid group or a sulfonic acid group, or —(CH$_2$)$_n$—R$_1$ may also be alkyl of 2 to 4 carbon atoms or 2,3-dihydroxy-propyl;
R$_2$ is an unsubstituted or monosubstituted heterocyclic radical selected from the group consisting of 3-pyridyl, 5-pyrimidinyl, 2-thienyl, 2-furylmethyl, 2-thienylmethyl, 2-imidazolylmethyl, 2-thiazolylmethyl, 3-pyridylmethyl or 5-pyrimidinylmethyl, where the substituent is chlorine, methyl, acetylamino, hydroxyl, methylsulfinyl, methylsulfonyl, aminocarbonyl or aminosulfonyl; and
E is hydrogen or a protective group which is easily removable in vitro or in vivo;
or, when E is hydrogen, a non-toxic, pharmacologically acceptable salt thereof formed with an inorganic or organic base.

2. A compound of claim 1, where
A, Het and R$_2$ have the meanings defined in claim 1; and
E is benzyl, diphenylmethyl, trityl, tert. butyl, 2,2,2-trichloro-ethyl, trimethylsilyl or (alkanoyl of 1 to 5 carbon atoms)oxy(alkyl of 1 to 3 carbon atoms).

3. A compound of claim 1, which is sodium 7β-{D-α-[3-(4-hydroxy-2-(3′-pyridylmethylamino)-5-pyrimidinyl)-ureido]-p-hydroxyphenyl-acetamido}-3-{[1-(2′-hydroxyethyl)-tetrazol-5-yl]-thiomethyl}-ceph-3-em-4-carboxylate.

4. A compound of claim 1, which is sodium 7β-{D-α-[3-(2-(5′-aminosulfonyl-2′-thienylmethylamino)-4-hydroxy-5-pyrimidinyl)-ureido]-p-hydroxy-phenylacetamido}-3-{[1-(2′-hydroxyethyl)-tetrazol-5-yl]-thiomethyl}-ceph-3-em-4-carboxylate.

5. A compound of claim 1, which is sodium 7β-{D-α-[3-(2-(5′-aminosulfonyl-2′-thienylmethylamino)-4-hydroxy-5-pyrimidinyl)-ureido]-p-hydroxy-phenylacetamido}-3-[(1-vinyl-tetrazol-5-yl)-thiomethyl]-ceph-3-em-4-carboxylate.

6. A compound of claim 1, which is sodium 7β-{D,L-α-[3-(2-(5′-aminosulfonyl-2′-thienylmethylamino)-4-hydroxy-5-pyrimidinyl)-ureido]-2-thienylacetylamido}-3-{[1-(2′-hydroxyethyl)-tetrazol-5-yl]-thiomethyl}ceph-3-em-4-carboxylate.

7. A compound of claim 1, which is sodium 7β-{D-α-[3-(4-hydroxy-2-(4′-methyl-2′-imidazolylmethylamino)-5-pyrimidinyl)-ureido]-p-hydroxy-phenylacetamido}-3-{[1-(2′-hydroxyethyl)-tetrazol-5-yl]-thiomethyl}-ceph-3-em-4-carboxylate.

8. A compound of claim 1, which is sodium 7β-{D-α-[3-(2-(5′-aminosulfonyl-2′-thienylmethylamino)-4-hydroxy-5-pyrimidinyl)-ureido]-p-hydroxy-phenylacetamido}-3-{[1-(2′-aminocarbonylethyl)-tetrazol-5-yl]-thiomethyl}-ceph-3-em-4-carboxylate.

9. A compound of claim 1, which is sodium 7β-{D-α-[3-(2-(2′-furylmethylamino)-4-hydroxy-5-pyrimidinyl)-ureido]-p-hydroxyphenyl-acetamido}-3-{[1-(2′-methyl-sulfonylethyl)-tetrazol-5-yl]-thiomethyl}-ceph-3-em-4-carboxylate.

10. An antibiotic pharmaceutical composition consisting essentially of an inert pharmaceutical carrier and an effective antibiotic amount of a compound of claim 1.

11. The method of inhibiting the growth of or destroying bacteria in a warm-blooded animal, which comprises perorally or parenterally administering to said animal an effective antibiotic amount of a compound of claim 1.

* * * * *

UNITED STATES PATENT AND TRADEMARK OFFICE
CERTIFICATE OF CORRECTION

PATENT NO. : 4,401,667
DATED : August 30, 1983
INVENTOR(S) : BERND WETZEL ET AL.

It is certified that error appears in the above-identified patent and that said Letters Patent is hereby corrected as shown below:

Column 2, line 9: "pivaloylox-" should be -- pivaloyloxy- --.
        line 10: "ymethyl" should be -- methyl --.
Column 2, line 18: "substituen-" should be -- substituent --.
        line 19: Delete "t".
Column 11, line 50: "thos" should be -- those --.
Column 13, line 9: "palladium" should be -- pallidum --.
Column 13, line 18: Delete "t".
        line 19: "hienylmethylamino" should be
                -- thienylmethylamino --.
Column 14, line 40: "thienylm" should be -- thienyl- --.
        line 41: "ethylamino" should be -- methylamino --.

Signed and Sealed this

Thirty-first Day of July 1984

[SEAL]

Attest:

GERALD J. MOSSINGHOFF

Attesting Officer     Commissioner of Patents and Trademarks